United States Patent [19]
Innerfield

[11] 3,960,669
[45] *June 1, 1976

[54] URINE DIAGNOSTIC TEST FOR FIBRINOLYTIC ACTIVITY

[75] Inventor: Irving Innerfield, Tenafly, N.J.

[73] Assignee: Association for Pharmacologic Research, Inc., New York, N.Y.

[ * ] Notice: The portion of the term of this patent subsequent to Dec. 10, 1991, has been disclaimed.

[22] Filed: Feb. 11, 1975

[21] Appl. No.: 549,113

Related U.S. Application Data

[63] Continuation-in-part of Ser. No. 323,603, Jan. 15, 1973, abandoned.

[52] U.S. Cl. ...................... 195/103.5 R; 195/66 B; 195/68; 195/99; 424/2
[51] Int. Cl.² ......................................... G01N 31/14
[58] Field of Search ............. 195/66 B, 99, 103.5 R, 195/68; 424/2; 23/230 B

[56] References Cited
UNITED STATES PATENTS
3,853,710   12/1974   Innerfield..................... 195/103.5 R

OTHER PUBLICATIONS
Matsushama et al., Simplified Method for Detecting Fibrinogen and its Derivatives by Tanned Red Blood Hemagglutination Inhibition Immune Assay. Chem. Abst., Vol. 72, 87898g 1970 (p. 159).

Flute, P. T. The Assessment of Fibrinolytic Activity in Blood, Brit. Med. Bull. vol. 20, No. 3, 1964 (pp. 195–199).

*Primary Examiner*—David M. Naff
*Attorney, Agent, or Firm*—Blum, Moscovitz, Friedman & Kaplan

[57] ABSTRACT

A test for maladies which cause deviations in the rate of production of fibrinolytic enzymes is carried out by adding controlled quantities of standardized thrombin and fibrinogen solutions to a urine specimen and noting the clotting time. Shortening of the clotting time from that measured with urine from healthy subjects indicates that the quantity of fibrin degradation products (FDP) in the blood is below normal. Increased production of such FDP may be due to the presence of a blood clot, an embolism, severe liver disturbance, cancer, extensive myocardial infarction, or pancreatic inflammatory disease. Conversely, decreased production of said FDP is taken as indicating a condition presaging the formation of a blood clot, or a significant decrease in the rate of production of fibrinolytic enzymes. The detection of either type of deviation can be used as the basis for diagnosis and treatment.

6 Claims, No Drawings

URINE DIAGNOSTIC TEST FOR FIBRINOLYTIC ACTIVITY

CROSS REFERENCE TO RELATED APPLICATION

This application is a continuation-in-part application of my co-pending application Ser. No. 323,603 filed Jan. 15, 1973, now abandoned, for URINE DIAGNOSTIC TEST FOR PATHOLOGIC FIBRINOLYTIC STATES.

BACKGROUND OF THE INVENTION

As is known, certain types of malfunctions of the human body are difficult to detect or require difficult and expensive procedures for the detection thereof. Blood clots are particularly pertinent examples, especially since they may presage a severe crisis in the individual involved. Pancreatic cancer is another example of a disturbance which is extremely difficult to diagnose without surgical exploration.

As aforenoted, the imminence of formation of a blood clot which may result in a coronary thrombosis and myocardial infarction is indicated by shortening of the clotting time due to a drop in the concentration of proteolytic enzymes and a consequent decrease in FDP.

Disturbances of the type with which the present invention is concerned have in common the property of changing the rate of production of fibrinolytic enzymes. Unfortunately, there has been, heretofore, no test for detection of a decrease in the concentration of such fibrinolytic enzymes and FDP in the blood. Consequently, it has been difficult to use the change in production of fibrinolytic enzymes as a basis for diagnosing the causative factors involved.

SUMMARY OF THE INVENTION

A thrombin solution is prepared, mixed with a standard fibrinogen solution which has been incubated at 37°C for 3 minutes and the clotting time at room temperature is measured. This serves to standardize the thrombin solution. The standardized thrombin solution with added standard fibrinogen is then tested for clotting time with reconstituted lyophilized normal urine. This establishes the normal clotting time for the standardized thrombin solution against normal urine.

Standardized thrombin is mixed at room temperature with fibrinogen solution which has been incubated at 37°C for 3 minutes with urine from a subject. The mean clotting time for healthy ambulent individuals is 35 seconds with a standard deviation of 8 seconds. Where the subject has in his urine a larger than normal quantity of FDP, the clotting time is appreciably lengthened, generally to above 43 seconds. A clotting time below 19 seconds is taken as a strong indication of a disturbance of the type which decreases the concentration of FDP in the blood and alerts the physicial to an incipient thrombotic episode, myocardial infarction, coronary thrombosis, transplant rejection or stroke.

A clotting time of 51 seconds or above is a strong indication of a significant increase in FDP and fibrinolytic activity in the blood, such an increase also requiring immediate medical treatment.

A thrombin solution suitable for use in the test described and having a long life at room temperature is prepared by adding thrombin to a solution of sodium oxalate, adding solid barium sulfate to adsorb any adsorbable materials introduced with the thrombin, separating off the barium sulfate by centrifugation and adding glycerol, trichloracetic acid (TCA) and normal saline. The materials adsorbed on the barium sulfate are of high molecular weight or are colloidal.

Accordingly, an object of the present invention is to provide a method of determining variation from the normal concentration of fibrinolytic enzymes and FDP in the blood of an individual.

Another object of the present invention is to provide a method of determining the presence in an individual of a malady of such a type as causes a change in fibrinolytic enzymes and FDP in the blood, such maladies including cancer, hepatitis, liver malfunction and blood clots, coronary thrombosis, cerebral thrombosis, deep vein thrombosis and pre-infarction syndrome.

A significant object of the invention is to provide a thrombin stock solution stable at room temperature for an extended period.

A particularly important objective of the invention is to provide a simple method of determining deviations from the normal quantity of fibrinolytic enzymes in the blood of a patient using urine from said patient.

Still other objects and advantages of the invention will in part be obvious and will in part be apparent from the specification.

The invention accordingly comprises the several steps and the relation of one or more of such steps with respect to each of the others, and the composition possessing the features, properties and the relation of constituents, which are exemplified in the following detailed disclosure, and the scope of the invention will be indicated in the claims.

DESCRIPTION OF THE PREFERRED EMBODIMENTS

In accordance with the present invention a urine specimen can be used for determination of the concentration of fibrinolytic enzymes and FDP in the blood. As the first step the clotting time for standardized solutions of thrombin and fibrinogen with reconstituted, lyophilized mixed urine from healthy subjects is determined where the fibrinogen solution and the urine have been incubated at 37°C for at least 3 minutes. The standardized reagents are then used with urine from a test subject or patient and the clotting time determined. The clotting time for the test subject is then compared with the range of clotting times determined with the reconstituted, lyophilized mixed urine. The basis for this test lies in the fact that fibrinolytic activity increases in the body in the presence of a clot or severe liver disturbance such as cirrhosis, liver cancer, hepatitis or in pancreatic inflammatory disease or pancreatic cancer and decreases in various types of pre-infarction syndrome, pulmonary embolism and strokes due to clots or emboli. Such conditions become evident through changes in the concentration of fibrinolytic enzymes and FDP in the blood; these FDP pass into the urine so that the concentration of such FDP in the urine is an indication of the concentration of fibrinolytic enzymes in the blood.

In normal urine, fibrinogen break-down products are present. In an abnormal condition, where fibrinolytic activity is increase in the blood, there will be an increase in fibrinolytic enzymes and fibrin and fibrinogen will be attacked in the blood to form FDP; the FDP accumulates very rapidly in the urine where they are competitive with plasma as substrates for the clotting reaction with the thrombin. In the absence of, or where there is a significant decrease of break-down products, the thrombin-fibrinogen reaction occurs rapidly and the clotting time on a urine sample is significantly shortened. When the concentration of FDP in the blood and consequently in the urine is above normal, the concentration of FDP in the urine will be increased and the clotting time will likewise be increased. The diagnostic test of the present invention is the reaction of thrombin with fibrinogen in a urine specimen to form clotted fibrin in the presence of FDP.

To utilize the diagnostic test of the present invention, it is necessary to set up standard conditions, these including standardized solutions and standard reaction conditions. The process by which the reagent solutions are standardized and the test is carried out involves the following steps.

THROMBIN STOCK SOLUTION (Unstable at room temperature)

Topical thrombin in solid form is available in vials from Parke-Davis, each vial containing 1,000 NIH units. The contents of a vial are dissolved in 150 ml of normal saline or distilled water. The material must be stored in an ice bath, and is stable for only a few hours.

THROMBIN STOCK SOLUTION (Stable at room temperature)

A 5,000 unit vial of Parke-Davis topical thrombin is dissolved in 1 ml of 2% sodium oxalate and 4 ml of normal saline. To this is added 500 mg of barium sulfate. The mixture is incubated at 37°C at 10 minutes and then centrifuged. The liquid is removed from the barium sulfate cake which holds whatever materials are adsorbable from the thrombin. The liquid is then mixed with 20 ml of normal saline and 25 ml of glycerol and 5 mg of TCA. This stock solution, which holds 100 NIH units per ml, is stable in excess of 6 months at room temperature.

For use, to one ml of a stock thrombin solution are added 14 ml of Veronal buffer (200 ml of 0.1M sodium barbital, 144 ml 0.1 N HCl, brought to 1 liter with normal saline and adjusted to pH 7.4 with additional sodium barbital, if necessary). Each ml has 6.67 NIH units therein. As is evident, other pharmaceutically acceptable buffers such as phosphate buffers or tris-(hydroxymethyl) aminomethane can also be used to bring the pH to 7.4.

The composition of the stable thrombin solution is not critical. For instance, the quantity of sodium oxalate can vary between about 100 mg and 1,000 mg. The incubation period may be between 5 and 15 minutes. Finally, from 15 to 35 ml of glycerol can be used with enough normal saline to bring the total volume up to 50 ml. Most important, the concentration of thrombin is intended to give a clotting time of 15 seconds with standard fibrinogen solution. The concentration can be changed at will to give longer or shorter clotting times as reference points.

FIBRINOGEN SOLUTION

A standardized stock solution of fibrinogen is prepared by adding 48 mg of Warner-Lambert plasma to 5 cc of normal saline. It is the fibrinogen content of said plasma which is the active constituent.

STANDARD URINE

Lyophilized normal urine is obtained from Lederle. This material is obtained from many subjects (pregnant women only) so that it represents the mean of a normal distribution. A standard urine solution is formed by adding 420 mg of the Lederle material to 25 ml of normal saline. The reconstituted urine is frozen for storage. Prior to use, the requisite quantity is thawed.

PROCEDURE

A number of preliminary tests are necessary to establish the performance of the various components before running a test on the urine of a patient. In the first of such tests, 0.2 ml of fibrinogen solution are placed in a test tube which is then incubated in a water bath at 37°C± 0.1°C for 3 minutes. The test tube is removed from the bath and to the tube is promptly added 0.1 ml of Veronal-buffered stabilized-thrombin solution; the test tube is tilted back and forth or otherwise moved so as to mix the components until clotting occurs. With solutions prepared as described above, the clotting time should be 15± 0.5 seconds. This test checks out both the procedure and the solutions. It should be noted that the mean clotting time for the Lederle urine is shorter than that for the generaly healthy population.

The second test which is actually a second control test is to add 0.1 ml of normal saline to 0.2 ml of standard fibrinogen solution in a test tube before putting same in the 37°C water bath. After incubation for 3 minutes, the test tube is removed from the bath and 0.1 ml of Veronal-buffered stabilized-thrombin solution is promptly added as before. The clotting time should be 17.5± 0.5 seconds. This test compensates for the saline in the reconstituted urine.

In the third control test, 0.1 ml of reconstituted lyophilized, mixed urine is substituted for the normal saline of the second test. The clotting time should be 35± 2 seconds.

The fourth control test constitutes the establishment of the range of clotting times to be expected with urine from individual healthy subjects. A test was run on urine from 100 control individuals ranging in age from 14 to 88 years, all of whom had been examined and found to be in such condition that a change in the concentration of fibrinolytic enzymes in the blood and consequently in the urine was not to be expected. The mean clotting time proved to be 35 seconds with a standard deviation of 8 seconds. The range was 25 to 54 seconds. In general, younger individuals tend to have slightly shorter clotting times than the older members of the group.

Tests were then run on patients having a variety of pathologies known to cause an increase in fibrinolytic enzymes in the blood. Fifty patients known to have pancreatic disturbances had an average clotting time of 20 seconds with a standard deviation of 2 seconds. The range was 17 to 23 seconds. Most of the patients fell in the range of 17 to 20 seconds. The diagnosis of pancreatic disturbance was established by serum amylase determination, surgical exploration, biopsy, autopsy and clinical picture.

Fifty patients known to have liver disturbances as confirmed by enzyme tests, liver function tests, autopsy and biopsy findings were subjected to similar tests. The average clotting time proved to be 18 seconds with a standard deviation of 1.2 seconds. The range was 17 to 22 seconds.

Twelve patients with recent strokes due to hemorrhage showed no decrease in clotting time. Apparently, therefore, hemorrhage dos not, of itself, give rise to an increase in fibrinolytic enzymes in the blood. In contrast, patients with thrombosis or embolism showed shortened clotting times.

The method of running a test on a subject or patient is exactly the same as described in the fourth control test except that 0.1 ml of the patients urine is used instead of the urine of the control test. It should be noted that the clotting time of the test patient is compared with the clotting time of the fourth control test which is based on urine from healthy subjects which shows a relatively wide deviation as compared to mixed urine. The clotting time of the patient is thus compared with a standard clotting time of 35±8 seconds. Consequently, any clotting time which deviates from the average by more than two standard deviations, i.e., less than 19 seconds which is the lower end of the range or above 51 seconds which is the upper end of the range, is taken as strongly indicative of a change in the concentration of fibrinolytic enzymes and FDP in the blood and therefore indicative of a disturbance or malady of such a type as to cause such an increase.

Although the mechanism believed to be responsible for changing the clotting time of urine from a test patient has been discussed above, the present invention is not to be considered as being limited by any specific mechanism. The test is based on change in the clotting time of urine when mixed with fibrinogen and buffered stabilized thrombin and on the positive correlation between change in the clotting time and the presence of certain types of illnesses. Furthermore, the concentrations of thrombin, and fibrinogen solutions and the relative quantities used with urine can be varied over a range, these variations resulting in a change in the standard clotting time with healthy subjects, such changes being readily made by one skilled in the art without going beyond the bounds of the present invention. Also, an incubation temperature of 37°C is used merely because most biochemical laboratories are provided with a bath at this temperature. However, as is evident, other temperatures could be used but the clotting times would have to be established for such other temperatures. Also, the 3 minute incubation period specified is a minimum only.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of detecting an abnormal concentration of fibrinolytic enzymes and fibrinogen degradation products in the blood of an individual, such an abnormal concentration being characteristic of certain pathologic states, comprising the steps of determining the average and the range of clotting times of standardized saline solutions of buffered thrombin, fibrinogen and urine from healthy subjects combined in selected proportions at a selected temperature, and determining the individual clotting time at the same selected temperature of the same standardized saline solutions of buffered thrombin and fibrinogen with a urine specimen from said individual combined in said selected proportions, an individual clotting time deviating by a selected amount from said average being taken as indicative of an abnormal concentration of fibrinolytic enzymes and fibrinogen degradation products in the blood and certain characteristic pathologic states.

2. The method as defined in claim 1, wherein said standardized solution of buffered thrombin comprises 6.7 NIH units per ml of normal saline.

3. The method as defined in claim 1, wherein said standardized buffered thrombin solution is prepared by adding 14 ml of a member selected from the group consisting of Veronal buffer, phosphate buffer and tris-(hydroxymethyl) aminomethane at pH 7.4 to 1 ml of a stock solution, said stock solution being prepared by the steps of mixing a 5000 unit vial of topical thrombin, 1 ml of 0.5 to 5% sodium oxalate, 4 ml of normal saline and a quantity of $BaSO_4$ sufficient to adsorb any colloidal or high molecular weight materials present, centrifuging said mixture, recovering the supernatent liquid and adding 20 ml of normal saline, 25 ml of glycerol and 5 mg of trichloracetic acid, the resultant solution being a stock solution stable in excess of 6 months at room temperature.

4. The method as defined in claim 3, wherein said standardized solution of fibrinogen is prepared by dissolving dried plasma in normal saline in the ratio of 48 mg to 5 ml.

5. The method as defined in claim 3, further comprising the steps of placing 0.2 ml of fibrinogen solution containing 48 mg of plasma per 5 ml of normal saline and 0.1 ml of urine from a healthy subject in a test tube, incubating at 37°C± 1°C for three minutes, removing said test tube from said bath, adding 0.1 ml of said buffered thrombin solution, and moving said test tube in such a way as to induce mixing until clotting occurs, the method being replicated, thereby determining the mean clotting time and the range of clotting time for urine from healthy subjects.

6. A method of determining the clotting time of the urine of an individual, comprising the steps of placing in a vessel 0.2 ml of said standardized fibrinogen solution prepared as defined in claim 4 and 0.1 ml of urine from said individual, incubating the vessel contents for at least 3 minutes in a bath at 37°C±0.1°C, removing said vessel from said bath, adding promptly 0.1 ml of said standardized buffered thrombin solution, and moving said vessel in such a manner as to mix the contents thereof until clotting occurs, a clotting time below 19 seconds or above 51 seconds being taken as indicative of certain types of maladies.

* * * * *